US011472835B2

(12) United States Patent
Kandukuri et al.

(10) Patent No.: US 11,472,835 B2
(45) Date of Patent: Oct. 18, 2022

(54) INTEGRATED AUTOMATED FILTRATION FOR SEPARATION, WASHING AND DRYING OF PEPTIDE CRYSTALS

(71) Applicant: BIOCON BiOLOGICS INDIA LIMITED, Bengaluru (IN)

(72) Inventors: Sai Srikar Kandukuri, Guntur (IN); Vibhava Shukla, Bengaluru (IN); Arul Marimuthu, Thanjavur (IN); Mukul Pathy, Bhubaneswar (IN); Partha P. Hazra, Bengaluru (IN)

(73) Assignee: BIOCON BIOLOGICS INDIA LIMITED

( * ) Notice: Subject to any disclaimer, the term of this patent is extended or adjusted under 35 U.S.C. 154(b) by 327 days.

(21) Appl. No.: 16/650,772

(22) PCT Filed: Sep. 19, 2018

(86) PCT No.: PCT/IB2018/057204
§ 371 (c)(1),
(2) Date: Mar. 25, 2020

(87) PCT Pub. No.: WO2019/064125
PCT Pub. Date: Apr. 4, 2019

(65) Prior Publication Data
US 2020/0223886 A1 Jul. 16, 2020

(30) Foreign Application Priority Data
Sep. 26, 2017 (IN) .............................. 201741034158

(51) Int. Cl.
*B01D 9/02* (2006.01)
*C07K 14/62* (2006.01)
(Continued)

(52) U.S. Cl.
CPC ............... *C07K 1/306* (2013.01); *C07K 1/34* (2013.01); *C07K 14/62* (2013.01); *F26B 5/14* (2013.01); *B01D 2009/009* (2013.01)

(58) Field of Classification Search
CPC .... A61K 38/28; B01D 37/0046; B01D 43/00; B01D 2009/009; C07K 1/306; C07K 1/34;
(Continued)

(56) References Cited

U.S. PATENT DOCUMENTS 2,920,014 A * 1/1960 Petersen ................ B01D 9/005
530/304
3,102,077 A * 8/1963 Christensen ........... C07K 14/62
530/304
(Continued)

FOREIGN PATENT DOCUMENTS

CN 103512318 A 11/2015
EP 2502633 A1 9/2012
(Continued)

*Primary Examiner* — Jeffrey E. Russel
(74) *Attorney, Agent, or Firm* — Marianne Fuierer; Casimir Jones, S.C.

(57) ABSTRACT

The present invention describes the integration of preparative crystallization, crystal separation, crystal washing and freeze-drying processes of insulin and insulin analogues into single continuous process using pressure filtration. The process facilitates time reduction and outlines the novel design of using multiple organic solvent washes and nitrogen gas purging for the removal of imbibed water and achieve final drug substance that meets the quality specifications.

10 Claims, 6 Drawing Sheets

(51) Int. Cl.
*F26B 5/14* (2006.01)
*C07K 1/30* (2006.01)
*C07K 1/34* (2006.01)
*B01D 9/00* (2006.01)

(58) Field of Classification Search
CPC ........ C07K 1/36; C07K 14/62; C07K 14/625; F26B 5/14
See application file for complete search history.

(56) References Cited

U.S. PATENT DOCUMENTS

| | | |
|---|---|---|
| 6,408,536 B1 | 6/2002 | Deusser et al. |
| 8,769,841 B2 | 7/2014 | Gruber et al. |
| 2014/0155574 A1 | 6/2014 | Wang et al. |
| 2017/0209545 A1 | 7/2017 | Watson et al. |

FOREIGN PATENT DOCUMENTS

| | | | | |
|---|---|---|---|---|
| EP | 2708550 A1 * | 3/2014 | ............. | C07K 1/306 |
| JP | 2002535415 A * | 10/2002 | | |
| WO | WO199640730 A1 | 12/1996 | | |
| WO | WO-2015084694 A2 * | 6/2015 | ........... | C07K 1/1136 |
| WO | WO2015084694 A2 | 6/2015 | | |
| WO | WO-2016032869 A1 * | 3/2016 | ............. | A61K 38/28 |
| WO | WO2016032869 A1 | 3/2016 | | |

* cited by examiner

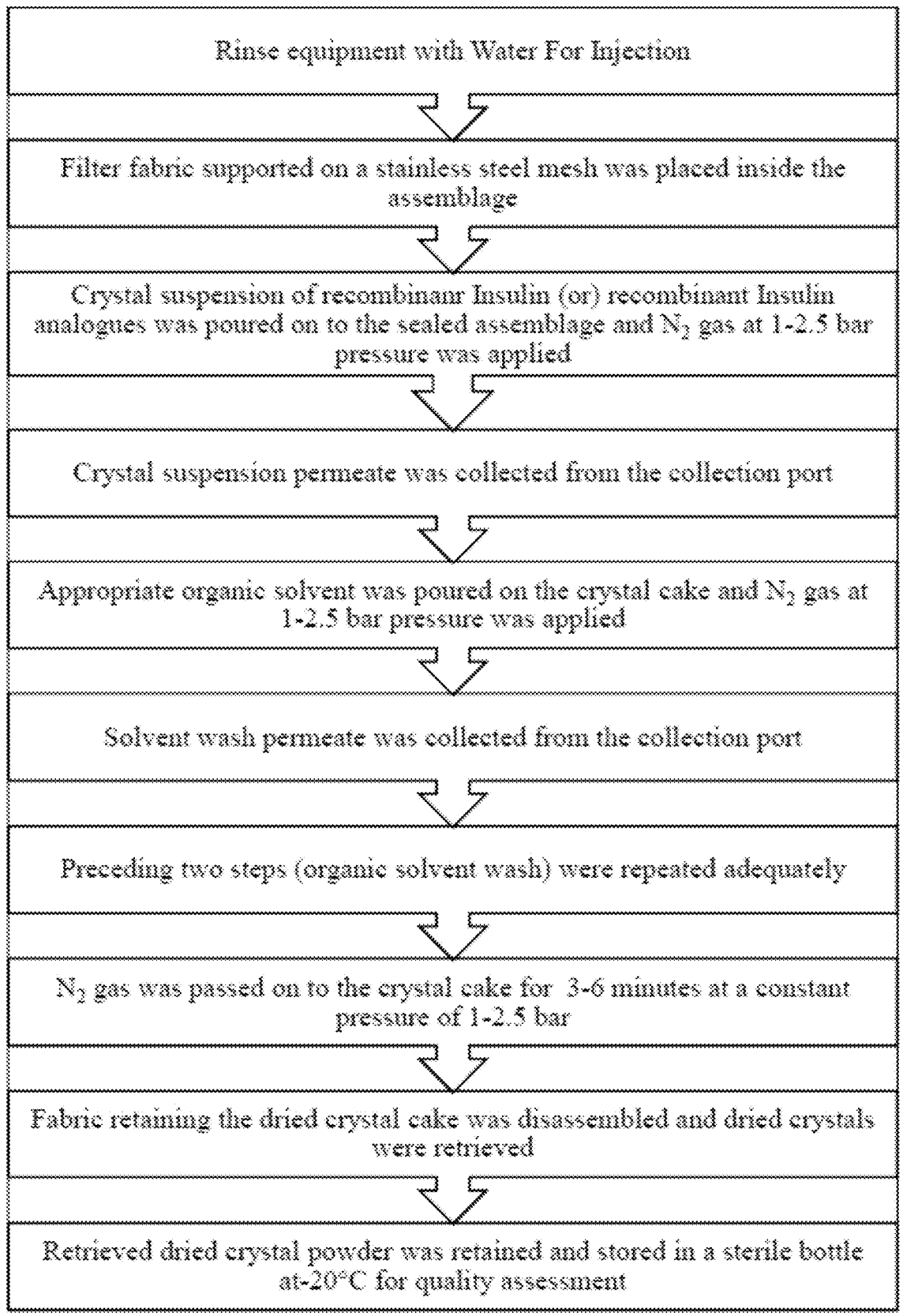
Figure 1: flowchart of process pressure filtration in rHI purification

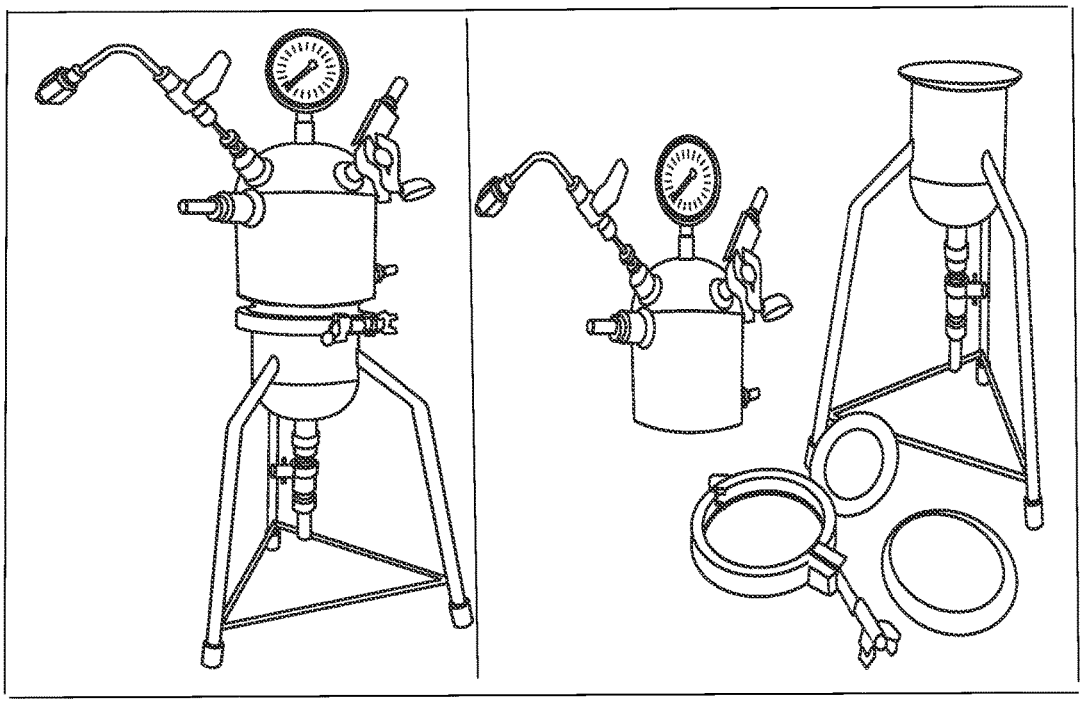
Figure 2: Representative image of lab scale pressure filter
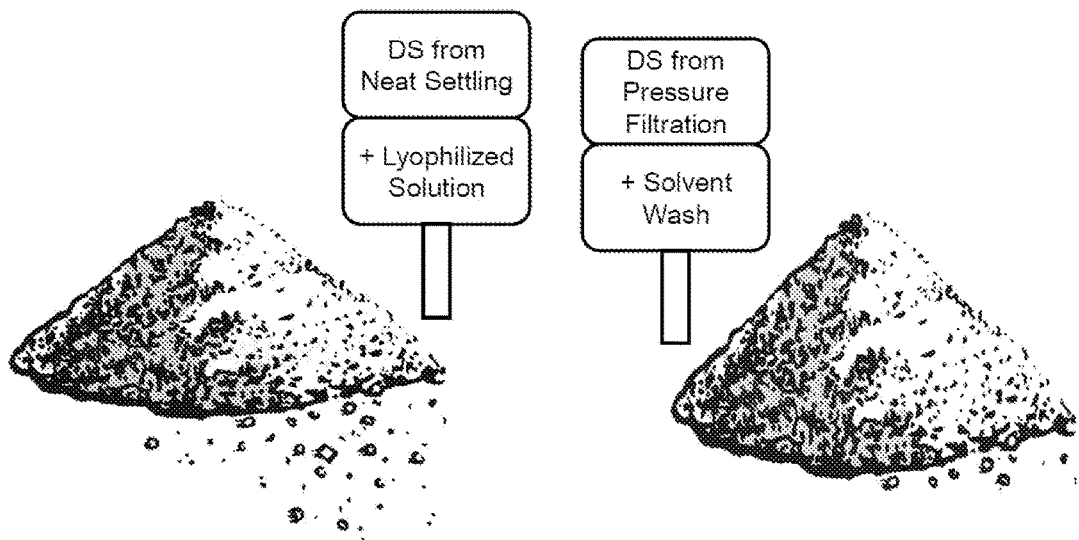
Figure 3: drug substance from conventional (left) and new (right) process

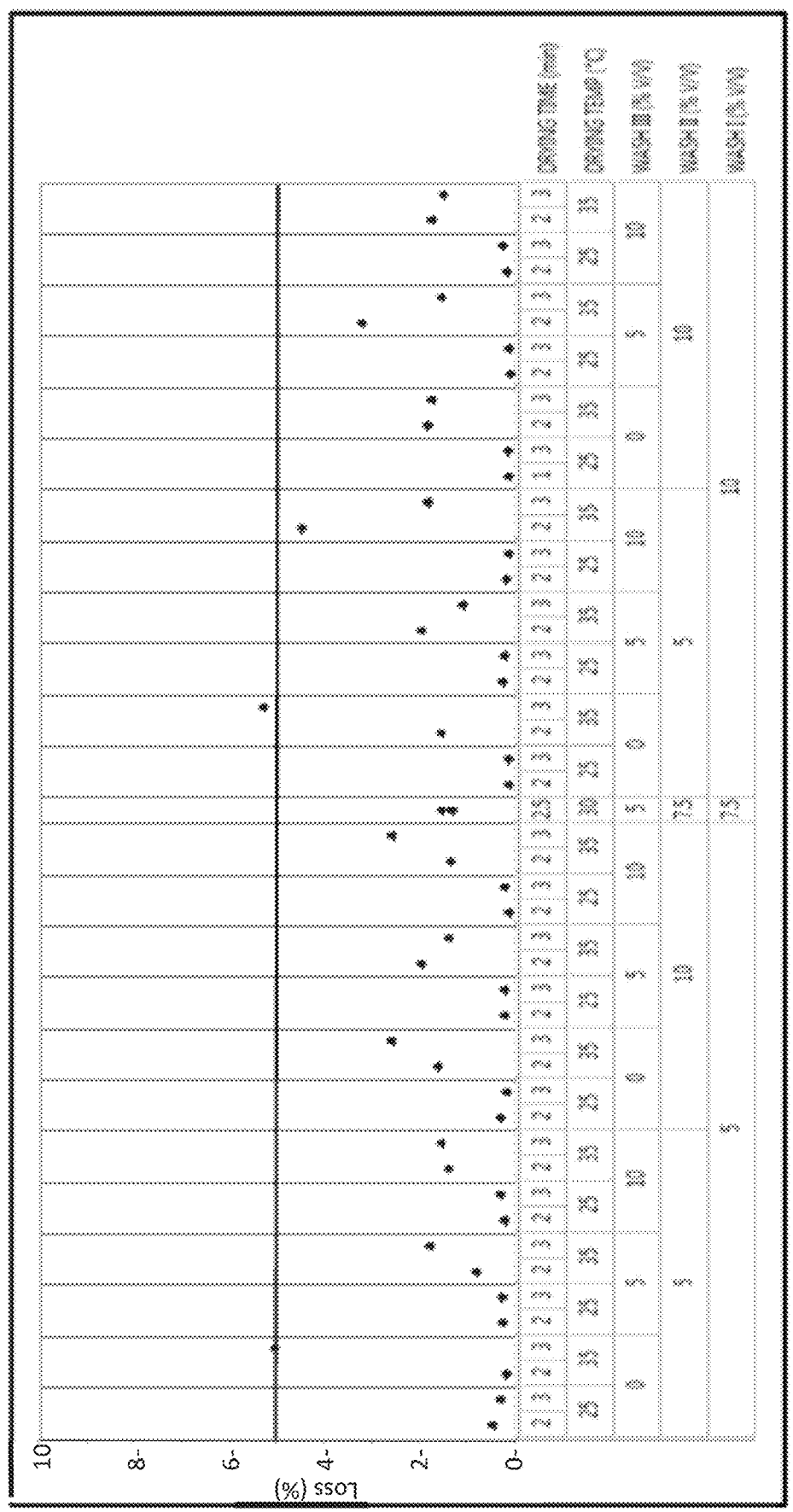

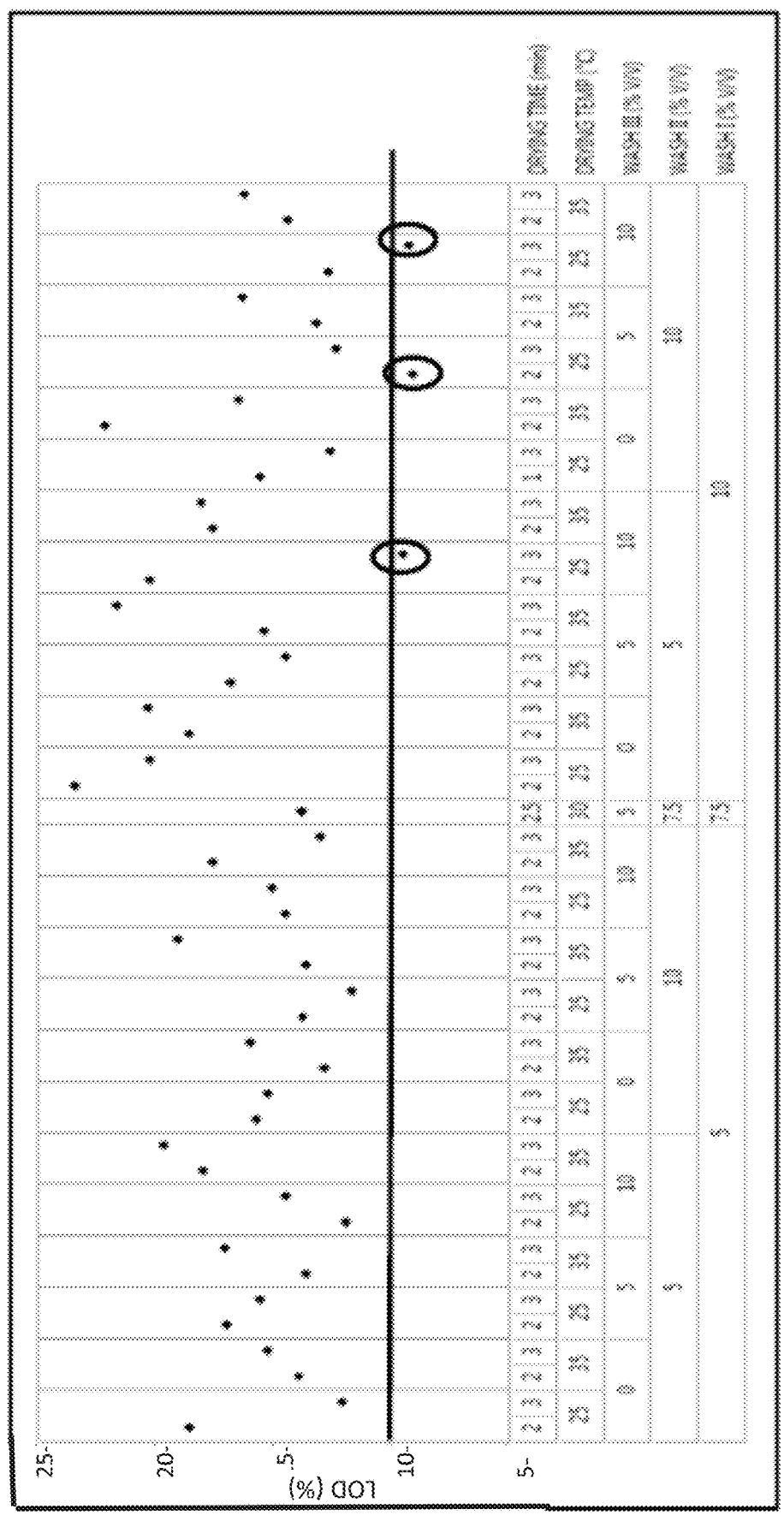
Figure 5: Variability chart for LOD %

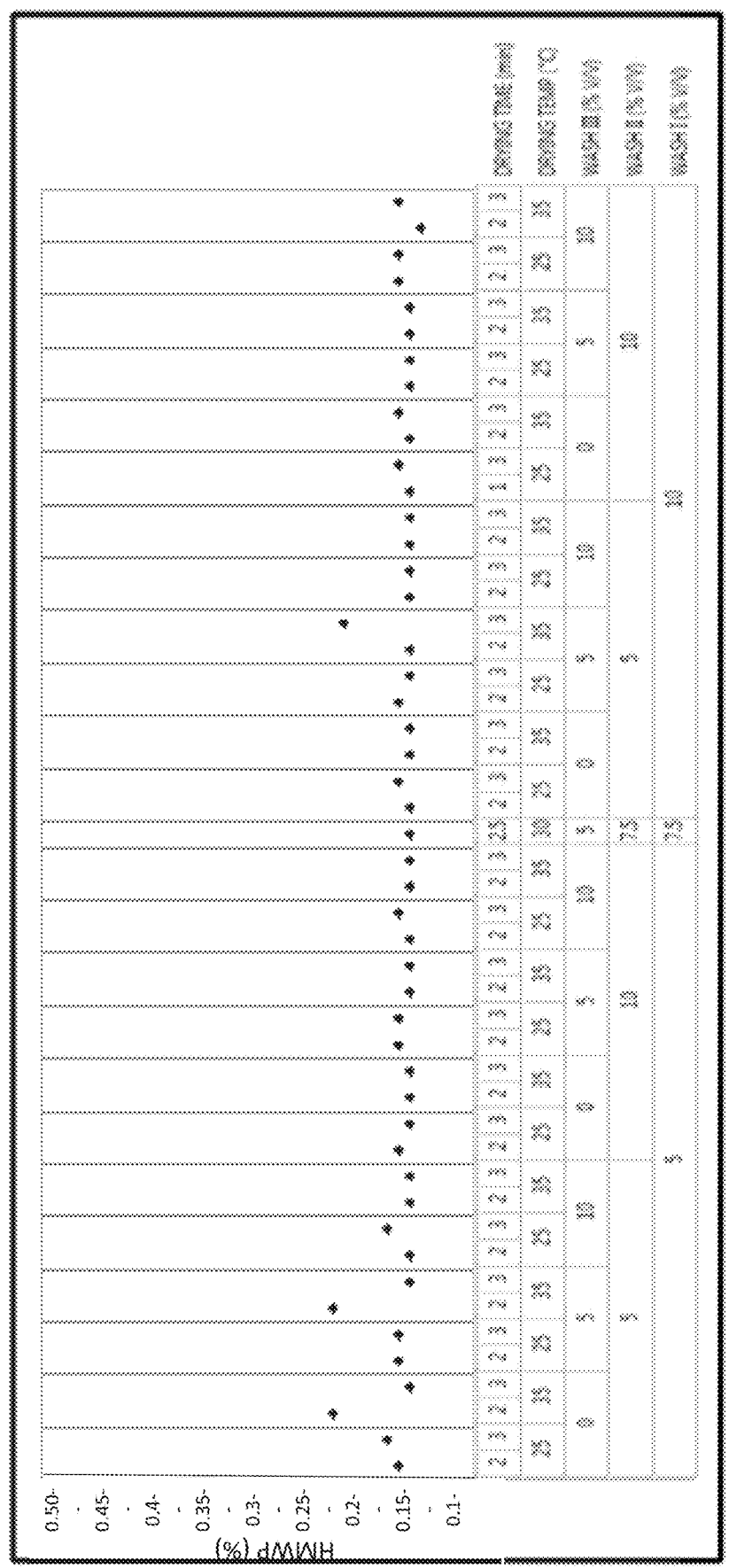
Figure 6: Variability chart for HMWP %

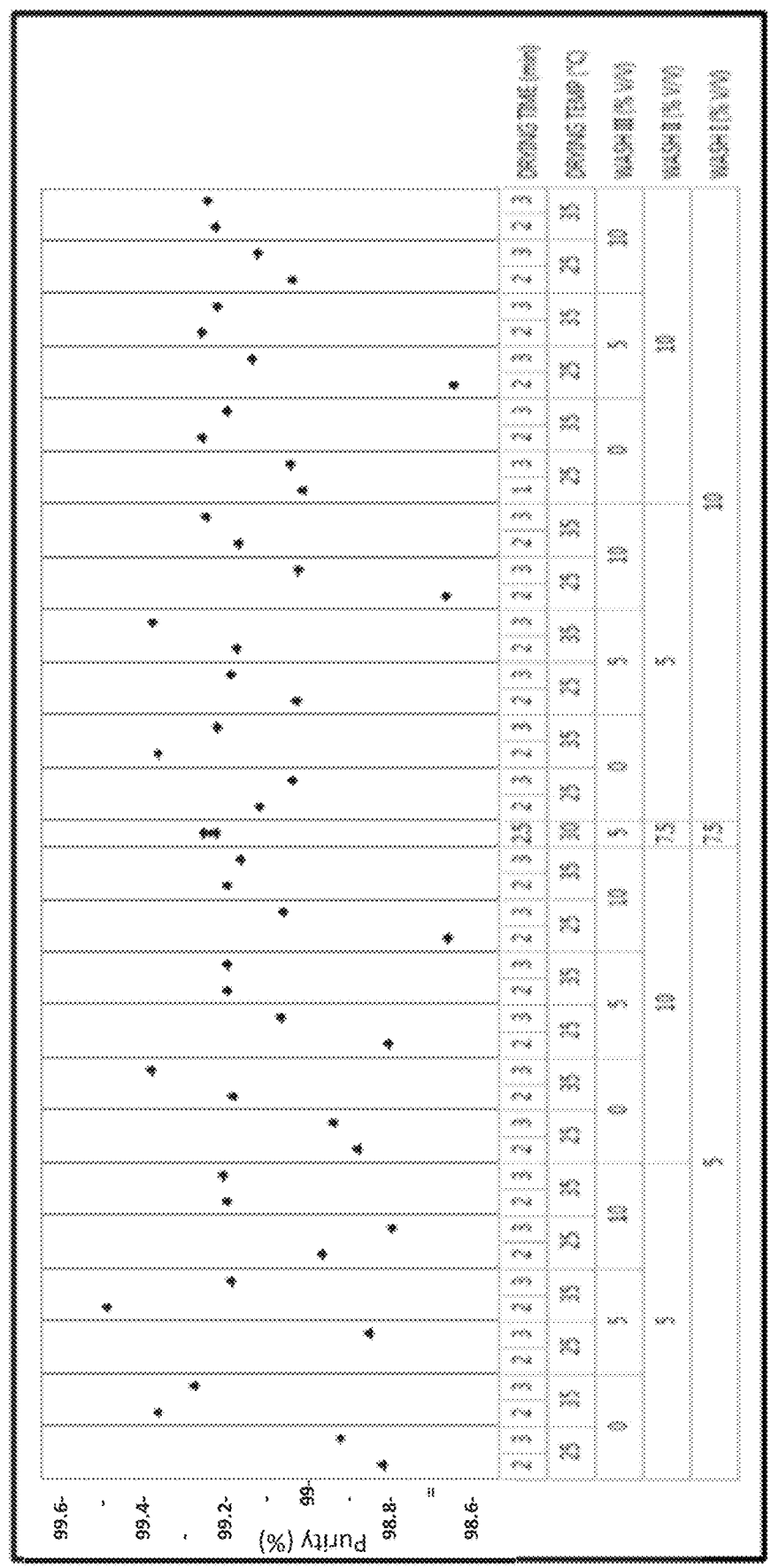
Figure 7: Variance chart for Purity %

INTEGRATED AUTOMATED FILTRATION FOR SEPARATION, WASHING AND DRYING OF PEPTIDE CRYSTALS

CROSS-REFERENCE

This application is filed under the provisional of 35 U.S.C. § 371 and claims the priority of International Application No. PCT/IB2018/057204, filed Sep. 19, 2018, which claims priority to IN Application No. 201741034158, filed Sep. 26, 2017.

FIELD OF INVENTION

Present invention relates to downstream processing of biologics, more specifically, to downstream processing of Insulin and its analogues. Present invention further relates to integration of crystal separation, followed by crystal washing and freeze-drying into a single continuous process for purification of insulin and its analogues.

BACKGROUND OF INVENTION

Traditionally, preparative protein crystallization involves a series of washing (of the settled crystals) and gravity settling steps. The end product of preparative protein crystallization is further processed by vacuum assisted freeze-drying to obtain the drug substance (DS) in dry powder form. The resultant drug substance must conform to purity by residual substance (RS) analysis, moisture content (LOD-Loss on Drying), sulphated ash content (ROI) and residual solvent limits as per universal quality and regulatory specifications. The entire process of preparative crystallization, settling of the crystals in the tank and washing to meet the desired quality requirements and freeze-drying requires a minimum of 7 days at commercial scale. Evidently, the discontinuous and modular nature of this process makes it energy, cost and time intensive.

Methods of crystallization and purification of insulin or insulin analogs have been disclosed in WO2015084694, U.S. Pat. No. 8,769,841, WO1996040730, CN103512318 and U.S. Pat. No. 6,408,536.

WO2015084694 describes a method for crystallizing insulin or insulin analogues under alkaline conditions and purifying the crystals by filtering through a filter and drying the crystals captured on the filter to produce crystalline insulin or insulin analogue crystal compositions. After crystallization, the entire volume of decanted crystal suspension is then transferred to a filter apparatus. The filter apparatus described in WO2015084694 is an agitated Nutsche filter, which have a stainless steel screen with a pore size about 5 μm.

U.S. Pat. No. 8,769,841 discloses a process of freeze drying of an essentially aqueous solution comprising at least one first step having a first temperature and pressure level (i.e. primary drying phase) and at least one second step having a second temperature and pressure level following the first step (i.e. secondary drying phase).

WO1996040730 disclose a method for recovering an acylated protein, those that resist recovery by precipitation or crystallization and subsequent filtration from aqueous solutions, as a powder. Acylated proteins are certain acylated proinsulins, insulins and insulin analogues. The method comprises of combination adjusting the aqueous solution to near the isoelectric pH of the protein and providing a suitable alcohol concentration to cause precipitation of the protein in the form of filterable particles at the adjusted pH.

CN103512318 disclose a drug purification drying process that relates to a lyophilized processing of insulin wherein the process discloses a freeze-drying process for insulin. The impurity content is lower than conventional technology. This process avoids the use of organic solvents, eliminating the potential adverse effects on people and the environment, and saving the drying time of 2-3 days and improve industrial productivity.

U.S. Pat. No. 6,408,536 disclose a process for drying protein crystals from an aqueous protein crystal suspension. The process comprises of filtering off the crystals from an aqueous suspension, washing the filter cake, spin-drying the same, drying the crystals in the fluidized bed with a stream of moistened nitrogen and emptying the dried crystals using a nitrogen pressure surge into a flanged container.

Though several methods are available for crystallizing insulin and its analogues, there is a need to develop an alternative method to have simple and optimized process of crystallization, washing and separation of the crystal as well as drying the same which can be practised in the industry in a bigger scale equipment which works on the same principle.

The present invention offers an integrated simple process for separation and drying of insulin and its analogues.

OBJECT OF INVENTION

The object of present invention is to integrate the discrete processes of crystallization, washing of the crystals and freeze-drying into a single continuous process using pressure filtration while achieving comparable standards of critical quality attributes and process performance attributes.

SUMMARY OF INVENTION

The present invention describes the integration of preparative Insulin and Insulin analogues crystallization, crystal separation and freeze-drying processes into single continuous process using pressure filtration. The process facilitates time reduction, and outlines the novel design of using multiple organic solvent washes and nitrogen gas purging for the removal of imbibed water and achieve final drug substance that meets the major quality specifications.

BRIEF DESCRIPTION OF DRAWINGS

FIG. 1 represents flowchart of process of pressure filtration for insulin and insulin analogues purification FIG. 2 represents representative image of lab scale pressure-filter FIG. 3 represents drug substance from conventional (left) and new (right) process FIG. 4 represents variability chart for Product loss/recovery as Loss %

FIG. 5 represents variability chart for residual moisture content in Drug Substance as LOD (loss on drying) %

FIG. 6 represents variability chart for High Molecular Weight Products (HMWP) %

FIG. 7 represents variance chart for Purity %

DETAILED DESCRIPTION OF INVENTION

Definitions

The term 'crystal suspension' refer to a volume of solution prepared by addition of Zinc Chloride ($ZnCl_2$) to insulin or insulin analogue followed by pH adjustment in the range of 4.5-8.5 using acid/alkali. Addition of zinc improves the physical stability of insulin by multimerization.

The term 'filter' refer to a simple set up that is similar to a 'Buchner funnel' with the pore size of filter membrane used varying between '1-15 μm' which does not involve any centrifugal force. The term 'pressure filtration' refer to a solid-liquid filtration aided by controlled pressure that pushes the solution against a filter membrane so that the solid substance (crystalline insulin and insulin analogue) is retained as a cake while the (organic solvent) mother liquor passes through as permeate. This exogenous pressure results in increased effective flow rate, high pressure gradient across the membrane and use of inert gas ensures stability to the finished product. Pressure filtration is an instantaneous process with an operating time of between 2-5 minutes on a lab scale and 45-60 minutes on an industrial scale.

The term 'insulin' or 'insulin analogue' refer to 51 amino acid peptide hormone used for treatment of diabetes. It also refers to other insulin related forms such as insulin precursor or insulin analogue precursor, intermediate insulin or insulin analogue molecules obtained during downstream processes.

DESCRIPTION OF INVENTION

Insulin and insulin analogues were expressed extracellularly using a recombinant *Pichia* based fermentation process. Transformed *Pichia pastoris* yeast strain are fermented in culture medium. The secreted Insulin or Insulin analogues were recovered by method of chromatography.

Insulin and insulin analogue was crystallized from the chromatography elution pool. It was further made into crystal suspension in presence of Zinc Chloride (ZnCl$_2$) and at an appropriate pH (in the range of 4.5 to 8.5) by addition of acid or alkali. Profile of crystal suspension (percentage solids, purity) was determined. The resultant insulin or insulin analogue crystals had high purity. Entire volume of crystal suspension was washed with water to remove the free precipitant used for crystallization and was taken forward for further processing of freeze drying.

The crystal suspension was first processed for separation through pressure filtration process to obtain the dried cake. This separation process is devoid of gravity and centrifugal force. The dried cake had imbibed water, which is removed by steps of washing by organic solvent and purging nitrogen gas through it.

The single continuous process can be depicted in following four steps.

1. Pressure Filtration of crystal suspension (initial separation of crystals)
2. Drying: washing with organic solvents for displacement of imbibed water
3. Drying: final purge of nitrogen to remove residual organic solvents
4. Automatic dispensing of dried powder in a cGMP environment.

Similar integration of crystal separation, washing and drying can be performed at multiple preceding crystallization step during the downstream processing of insulin and insulin analogues. The raw material(s), reagent(s) and equipment(s) were used as per listed below in table 1, 2 and 3 respectively.

TABLE 1 list of raw material

| Sr. No. | Raw Materials | Grade | Manufacturer |
|---|---|---|---|
| 1. | Acetic acid | HPLC | Rankem |
| 2. | Acetonitrile (ACN) | HPLC | Rankem |
| 3. | Acetonitrile (ACN) | Commercial Grade | ASAHI KASEI |
| 4. | L-Arginine | Reagent grade | Sigma-Aldrich |
| 5. | 1-butanol | Commercial Grade | Deepak fertilizers |
| 6. | Ethanol | Commercial Grade | Changshu Yangyuan Chemicals |
| 7. | Ethyl acetate | Commercial Grade | Lakshmi Organic Industries |
| 8. | Filter membrane | Not Applicable | Sefar Filtration (India) Pvt. Ltd |
| 9. | HCl | ACS Reagent | Sigma-Aldrich |
| 10. | Methanol | Commercial Grade | Deepak fertilizers |
| 11. | 2-propanol | Commercial Grade | Deepak fertilizers |
| 12. | Trifluoroacetic acid | Chromasolv | Sigma-Aldrich |
| 13. | Water for injection | Not Applicable | Biocon |

TABLE 2 list of buffer/reagents and preparation

| Sr. No. | Buffers/Reagents | Preparation |
|---|---|---|
| 1. | 0.1% TFA in MilliQ water | Measure 1000 mL of MilliQ water. Pipette out 1 mL of water and add 1 mL of HPLC grade TFA. |
| 2. | 1N HCl | Measure 70 mL of water and then add 8.212 mL of concentrated HCl (HPLC grade). Make up the final volume to 100 mL using MilliQ water in a volumetric flask. |
| 3. | 0.01N HCl | Measure 245 mL of water. Add 2.5 mL of 1N HCl (HPLC grade). Make up the volume to 250 mL with MilliQ water. |
| 4. | HMWP buffer (High Molecular Weight Transfer buffer) | Measure 600 mL of milliQ water. Add 0.65 g of Reagent grade L-Arginine while on stirring. Make up the volume to 650 mL. Add 150 mL of Acetic acid and 200 mL of ACN. Filter the solution using a 0.45 μm followed by 0.2 μm filter and sonicate for 20 minutes. |

TABLE 3

List of equipment/instruments

| Sr. No. | Name | Model/Make |
|---|---|---|
| 1. | Analytical HPLC | Agilent HPLC- 1200/Agilent technologies Agilent HPLC- 1100/Agilent technologies LC-2010CHT/Shimadzu |
| 2. | Column | Advanced Chromatography Technologies: ACE 300-C18, 5 μm; 4.6 × 250 mm Waters: Insulin HMWP 7.8 × 300 mm |
| 3. | Pressure filter | Prototype from BHS Sonthofen |
| 4. | Vacuum oven | Servewell |
| 5. | Weighing balance | Mettler Toledo |
| 6. | Water bath | Julabo |
| 7. | Water bath | Equitron |
| 8. | Sonicator | Servewell |
| 9. | Vortexer | Shalom |
| 10. | Nitrogen Gas cylinder | Biocon |
| 11. | Cold room | Blue star |
| 12. | Deep freezer | Vestfrost |

The trials were performed in a lab scale pressure filter set up with an approximate filter cross-sectional area of 80 cm$^2$ to 100 cm$^2$. It also comprises of a pressure inlet for compressed inert gas (Nitrogen), a pressure gauge and safety release valve, sample inlet and outlet ports and a water jacket (FIG. 2).

Variable parameters were wash solvent, solvent volume, number of washes, time of nitrogen purging for each wash and an optional change of filter media, which is dependent on the size of crystals being processed. Process performance and quality attributes of the obtained drug substance were measured by analysing percentage of loss of crystals in permeate and loss on drying (LOD), purity and molecular weight (HMWP). The temperature of the set up was maintained in range of 25° C. to 35° C.

The cake formed by process of pressure filtration of insulin and insulin analogue crystal suspension, had requisite thickness and texture. However, the goal was to dry the cake to achieve acceptable standards of LOD and very importantly to integrate the crystallization-freeze drying of the conventional process into a single continuous process. To achieve sufficient displacement of imbibed residual water from filter cake, single or multiple wash strategies with different organic solvents were studied. The wash steps were also designed to enable effective removal of precipitants, and residual solvents that are present in reverse phase (chromatography) elution pool and obtain a drug substance that complies with the universal quality and regulatory specifications.

The assembly of instrument(s) for achieving the dried powder in continuous and automated manner was as follows:

i. The equipment was an SS cylindrical assemblage with jacketing to maintain required internal temperature as well as provision for passing an (inert) gas. Nitrogen gas cylinder and Julabo water chiller were used for these trials. The temperature was maintained in the range of 25-35° C.

ii. A filter fabric of 80 cm² to 100 cm² area was placed on an SS mesh support and housed in the assemblage. Fabric filter was selected from PET 1703 (Poly ester fabric) and SK-011 (Poly propylene fabric).

iii. The assemblage was sealed with a SS disc lined with silicon gasket, and clamps were fastened to make the compartment airtight, followed by pouring the homogenous neat suspension from the top of the vessel to commence pressure filtration.

iv. Nitrogen gas at bar pressure in the range of 1 bar to 2.5 was applied via NRV/inlet port.

v. Filtrate/permeate was collected via the sample outlet port at the bottom.

vi. Steps 'iii' and 'iv' were repeated for single or multiple cake washes using organic solvent.

vii. Drying was performed by addition of an organic solvent and further passing $N_2$ gas for about three minutes after which the assemblage was unfastened.

viii. The fabric containing the cake was carefully removed and gently tapped to recover the cake which was then transferred into a sterile airtight amber colour container and stored at −20° C. until further analysis.

Two trials were conducted. First, was preliminary screening (Trial I) and second (Trail II) was design of experiment (DOE).

Preliminary screening trials (trial 1) were performed in a lab scale prototype of industrial pressure filter (FIG. 2) with different organic solvents using the design described in Table 4. In preferable embodiment, acetonitrile was considered best working organic solvent. Filter fabrics were studied and screened for their pore size, i.e. retention of crystals, texture, workability on commercial scale and resilience/inertness to the pH and temperature conditions of the process. Two types of filter fabric were used viz. poly ester fabric and poly propylene fabric. Organic solvents were chosen based on their ability to displace water from the cake and their volatile nature (table 4). The FDA guidelines to acceptable solvents and their residual limits in final drug substance were also considered for the selection of solvents.

TABLE 4

Solvent screening design

| Trial number | Solvent | % Solvent volume based on crystal suspension volume | Washes |
|---|---|---|---|
| 1. | Acetonitrile (ACN) | 5 | 1 |
| 2. | | 5 | 2 |
| 3. | | 10 | 1 |
| 4. | Butanol | 5 | 1 |
| 5. | | 5 | 2 |
| 6. | | 10 | 1 |
| 7. | Ethanol | 5 | 1 |
| 8. | | 5 | 2 |
| 9. | | 10 | 1 |
| 10. | Ethyl acetate | 5 | 1 |
| 11. | | 5 | 2 |
| 12. | | 10 | 1 |
| 13. | Isopropanol | 5 | 1 |
| 14. | | 5 | 2 |
| 15. | | 10 | 1 |
| 16. | Water | 5 | 1 |
| 17. | | 5 | 2 |
| 18. | | 10 | 1 |

Solvents and wash combinations yielding high percentage LOD (loss on drying) values in the above design were eliminated. Data set is presented in table 5 and table 6.

The captured data set in table 5 and table 6 suggested that the resultant insulin and insulin analogue drug substance has comparable quality attributes to the drug substance made from traditional crystallization-freeze drying process with optimal recovery of product (FIG. 3).

Two washes of acetonitrile planned in Trail I has satisfactory outcome with respect to percentage LOD. However, to fall in-line with regulatory requirements a further reduction in LOD was desired. Parameters that were studied in this experimental setup included a) number of washes; b) drying time and c) temperature during filtration to study the probability of temperature accelerating the evaporation of the residual organic solvent trapped in filter cake. For Trail II (DOE), HMWP was also determined.

TABLE 5

Solvent Screening Result

| Wash Solvent % | Crystallization 3 Neat suspension (NS) | | | Wash 1 (W1) | | Wash 2 (W2) | | Drying time (min) | DS weight (g) | LOD % |
|---|---|---|---|---|---|---|---|---|---|---|
| | NS conc. (g/L) | NS volume (mL) | NS permeate (mL) | W1 volume (mL) | W1 permeate (mL) | W2 volume (mL) | W2 permeate (mL) | | | |
| 16 Jan. 2017 | | | | | | | | | | |
| LP1-5%-W1 | 14.65 | 300 | 285 | 15 | 21 | NAP | NAP | 1.5 | 5.52 | 26 |
| LP1 5% W 1 & 2 | 14.65 | 300 | 290 | 15 | 13 | 15 | 17.5 | 1.5 | 5.26 | 20.46 |
| LB1-5%-W1 | 14.65 | 300 | 280 | 15 | 18 | NAP | NAP | 1.5 | 6.33 | 35.14 |
| LB1-5%-W 1 & 2 | 14.65 | 300 | 290 | 15 | 13.5 | 15 | 20 | 2.5 | 5.88 | 36.22 |
| LA-5%-W1 | 14.65 | 300 | 290 | 15 | 14.3 | NAP | NAP | 1.5 | 4.96 | 15.99 |
| LA-5%-W 1 & 2 | 14.65 | 300 | 295 | 15 | 12.5 | 15 | 13.5 | 1.5 | 4.88 | 9.34 |
| LA-10%-W1 | 14.65 | 300 | 290 | 30 | 29 | NAP | NAP | 2 | 5.3 | 21.25 |
| LP1-10%-W1 | 14.65 | 300 | 290 | 30 | 31.5 | NAP | NAP | 2 | 5.43 | 21.14 |
| LB1-10%-W 1 | 14.65 | 290 | 275 | 30 | 30 | NAP | NAP | 2 | 5.5 | 25.1 |
| LP1-5%-W1 | 14.65 | 200 | 190 | 10 | 9.7 | NAP | NAP | 1.5 | 3.81 | NAV |
| 19 Jan. 2017 | | | | | | | | | | |
| LE-5%-W 1 & 2 | 14.65 | 300 | 290 | 15 | 9.8 | 15 | 18 | 2 | 5.66 | 22.35 |
| LEA-5%-W1 | 14.65 | 300 | 290 | 15 | 21.5 | NAP | NAP | 2 | 7.07 | 37.84 |
| LEA-5%-W 1 & 2 | 14.65 | 300 | 290 | 15 | 9 | 15 | 9.6 | 2 | 6.67 | 34.11 |
| LEA 10% W 1 & 2 | 14.65 | 300 | 280 | 30 | 25 5 | 30 | 28 | 2 | 6.87 | 36.03 |
| LE-5%-W 1 & 2 T1 | 14.65 | 300 | 290 | 15 | 18.5 | 15 | 16 | 2 | 5.44 | 15.75 |
| LE-5%-W 1 & 2 T2 | 14.65 | 300 | 285 | 15 | 13 | 15 | 16.5 | 2 | 6.06 | 16.43 |
| LA-5%-W 1 & 2 T1 | 14.65 | 300 | 300 | 15 | 15 | 15 | 14 | 2 | 5.38 | 10.52 |
| LA-5%-W 1 & 2 T2 | 14.65 | 300 | 305 | 15 | 10 | 15 | 9.5 | 2 | 5.7 | 11.53 |

LOD values in BOLD are actual values, rest are theoretical values based on neat suspension product concentration.
LA: Acetonitrile, LP1: Isopropanol, LB1: Butanol, LEA: Ethyl acetate, NS: Neat suspension, W1/2; Wash 1 and Wash 2, T1/2; Trial 1 and Trial 2; LOD: Loss on drying; NAP: Not applicable, NAV: Not available A full factorial experimental design along with the response data is presented in table 6. Fifty experiments were performed discretely as below (table 6).

TABLE 6

Experimental design with response data

| Sr. No. | Wash I (% V/V) | Wash II (% V/V) | Wash III (% V/V) | Drying Temp (° C) | Drying Time (min) | % LOD | % Purity | % HMWP | % Loss |
|---|---|---|---|---|---|---|---|---|---|
| 1 | 5 | 10 | 5 | 35 | 3 | 19.18 | 99.20 | 0.158 | 1.41 |
| 2 | 10 | 10 | 0 | 35 | 2 | 22.23 | 99.25 | 0.163 | 1.89 |
| 3 | 10 | 5 | 10 | 35 | 2 | 17.66 | 99.18 | 0.159 | 4.50 |
| 4 | 10 | 10 | 5 | 35 | 3 | 16.38 | 99.22 | 0.162 | 1.59 |
| 5 | 10 | 10 | 10 | 25 | 2 | 12.77 | 99.06 | 0.167 | 0.19 |
| 6 | 5 | 5 | 0 | 25 | 2 | 18.70 | 98.86 | 0.173 | 0.49 |
| 7 | 7.5 | 7.5 | 5 | 30 | 2.5 | 13.90 | 99.25 | 0.156 | 1.58 |
| 8 | 10 | 10 | 10 | 35 | 3 | 16.37 | 99.24 | 0.165 | 1.54 |
| 9 | 5 | 10 | 10 | 35 | 3 | 13.06 | 99.17 | 0.158 | 2.62 |
| 10 | 5 | 10 | 10 | 25 | 2 | 14.60 | 98.72 | 0.162 | 0.17 |
| 11 | 5 | 5 | 10 | 25 | 2 | 11.99 | 99.00 | 0.163 | 0.24 |
| 12 | 10 | 10 | 5 | 25 | 2 | 9.14 | 98.71 | 0.158 | 0.13 |
| 13 | 10 | 10 | 5 | 35 | 2 | 13.25 | 99.26 | 0.164 | 3.25 |
| 14 | 5 | 5 | 0 | 35 | 2 | 14.01 | 99.35 | 0.225 | 0.23 |
| 15 | 10 | 5 | 5 | 35 | 3 | 21.74 | 99.11 | 0.218 | 1.11 |
| 16 | 5 | 5 | 5 | 25 | 3 | 15.66 | 98.89 | 0.171 | 0.31 |
| 17 | 10 | 5 | 5 | 25 | 3 | 14.60 | 99.19 | 0.164 | 0.25 |
| 18 | 10 | 5 | 0 | 25 | 3 | 20.36 | 99.06 | 0.169 | 0.18 |
| 19 | 10 | 10 | 0 | 35 | 3 | 16.58 | 99.20 | 0.172 | 1.78 |
| 20 | 5 | 5 | 0 | 25 | 3 | 12.13 | 98.95 | 0.176 | 0.34 |
| 21 | 5 | 5 | 10 | 25 | 3 | 14.58 | 98.84 | 0.181 | 0.33 |
| 22 | 10 | 10 | 10 | 35 | 2 | 14.47 | 99.22 | 0.152 | 1.78 |
| 23 | 10 | 5 | 10 | 25 | 3 | 9.56 | 99.04 | 0.164 | 0.15 |
| 24 | 10 | 10 | 0 | 25 | 2 | 15.70 | 99.03 | 0.158 | 0.16 |
| 25 | 5 | 10 | 0 | 25 | 3 | 15.35 | 98.97 | 0.164 | 0.19 |
| 26 | 10 | 5 | 5 | 35 | 2 | 15.54 | 99.18 | 0.157 | 1.99 |
| 27 | 5 | 10 | 0 | 35 | 3 | 16.10 | 99.37 | 0.159 | 2.61 |
| 28 | 5 | 10 | 0 | 35 | 2 | 12.93 | 99.19 | 0.157 | 1.66 |
| 29 | 10 | 10 | 0 | 25 | 3 | 12.66 | 99.06 | 0.165 | 0.18 |
| 30 | 5 | 5 | 10 | 35 | 2 | 18.12 | 99.20 | 0.160 | 1.42 |
| 31 | 5 | 5 | 0 | 35 | 3 | 15.35 | 99.27 | 0.159 | 5.10 |

TABLE 6-continued

Experimental design with response data

| Sr. No. | Wash I (% V/V) | Wash II (% V/V) | Wash III (% V/V) | Drying Temp (° C) | Drying Time (min) | % LOD | % Purity | % HMWP | % Loss |
|---|---|---|---|---|---|---|---|---|---|
| 32 | 10 | 5 | 5 | 25 | 2 | 16.88 | 99.05 | 0.166 | 0.28 |
| 33 | 5 | 5 | 5 | 25 | 2 | 17.11 | 98.53 | 0.170 | 0.30 |
| 34 | 10 | 10 | 10 | 25 | 3 | 9.33 | 99.14 | 0.166 | 0.28 |
| 35 | 10 | 5 | 10 | 25 | 2 | 20.35 | 98.73 | 0.162 | 0.22 |
| 36 | 5 | 10 | 5 | 35 | 2 | 13.63 | 99.19 | 0.161 | 2.02 |
| 37 | 10 | 5 | 0 | 35 | 2 | 18.68 | 99.35 | 0.159 | 1.57 |
| 18 | 10 | 5 | 0 | 25 | 2 | 23.54 | 99.13 | 0.164 | 0.16 |
| 39 | 5 | 5 | 5 | 35 | 3 | 17.18 | 99.19 | 0.158 | 1.83 |
| 40 | 5 | 10 | 10 | 25 | 3 | 15.21 | 99.08 | 0.169 | 0.24 |
| 41 | 5 | 10 | 5 | 25 | 2 | 13.80 | 98.85 | 0.165 | 0.27 |
| 42 | 5 | 10 | 5 | 25 | 3 | 11.79 | 99.08 | 0.168 | 0.25 |
| 43 | 10 | 5 | 10 | 35 | 3 | 18.13 | 99.25 | 0.157 | 1.87 |
| 44 | 5 | 10 | 10 | 35 | 2 | 17.66 | 99.20 | 0.158 | 1.39 |
| 45 | 5 | 10 | 0 | 25 | 2 | 15.81 | 98.92 | 0.171 | 0.33 |
| 46 | 5 | 5 | 10 | 35 | 3 | 19.76 | 99.21 | 0.161 | 1.60 |
| 47 | 7.5 | 7.5 | 5 | 30 | 2.5 | 13.81 | 99.23 | 0.159 | 1.32 |
| 48 | 10 | 10 | 5 | 25 | 3 | 12.42 | 99.15 | 0.162 | 0.16 |
| 49 | 10 | 5 | 0 | 35 | 3 | 20.44 | 99.22 | 0.158 | 5.33 |
| 50 | 5 | 5 | 5 | 35 | 2 | 13.68 | 99.25 | 0.225 | 0.83 |

The drug, substance from Trials 12, 23 and 34 had the lowest LOD values i.e. of less than 10% (table 7), while drug substance from trials 11 and 42 had LOD values less than 12%. There were no significant changes in purity and HMWP profiles, and per-step losses were found to be well within range.

The results of variability are also represented in FIGS. 4, 5, 6 and 7 for percentage loss of product, percentage LOD, percentage HMWP and percentage purity respectively,

TABLE 7

Summary of results of DOE (Trial II)

| Trial number | WASHES (% V/V) | | | % LOD |
|---|---|---|---|---|
| | W I | W II | W III | |
| 12 | 10 | 10 | 5 | 9.14 |
| 23 | 10 | 5 | 10 | 9.56 |
| 34 | 10 | 10 | 10 | 9.33 |

From the multivariate studies, it was found out that more number of washes with organic solvent (3>2>1) resulted in ample displacement of imbibed water from filter cake. Three washes including wash 1 at 10%, wash 2 at 5% or 10% and wash 3 at 5% or 10%, were found to be most effective in reducing LOD. Volume of washes can be fine-tuned further as per process requirements. Increased drying time helped in forcing out some solvent imbibed in the cake post-washing. Increasing the temperature during filtration did not reduce the LOD of the drug substance, but it did not significantly affect the profile of the drug substance either. Thus, the temperature was maintained in the range of 25° to 35° C. Based on this multivariate study further trials can be designed and executed to further reduce the LOD to <4%.

The results of this multivariate study were satisfactory and drew immediate attention to a novel process that is shorter, continuous, less resource intensive and automated.

The invention claimed is:

1. An integrated process of crystal separation, washing and drying of insulin or insulin analogues, comprising the steps of:

a) preparing a crystal suspension of insulin or insulin analogue using Zn $Cl_2$ and adjusting the pH of the crystal suspension to between 4.5 and 8.5;

b) pouring the crystal suspension obtained from step a) onto a filter fabric placed on an area ranging between 80 $cm^2$ to 100 $cm^2$ of a pressure filtration unit;

c) purging the pressure filtration unit with nitrogen gas via an inlet port of the pressure filtration unit to obtain a filter cake;

d) collecting a filtrate via outlet port of the pressure filtration unit;

e) pouring 100% acetonitrile, butanol, ethanol, ethyl acetate or isopropanol as a solvent wash on the filtrate and purging nitrogen gas via an inlet port of the pressure filtration unit at a pressure of 1 to 2.5 bar;

f) collecting the filtrate via an outlet port of the pressure filtration unit;

g) repeating steps e) and f) to provide further solvent washes on the filtrate and thereby providing a filter cake;

h) drying the filter cake by passing nitrogen gas through the filter cake at a pressure range of 1 bar to 2.5 bar; and i) removing the filter cake in the form of a dried powder, wherein the process is conducted as a single continuous process.

2. The integrated process of claim 1, wherein the insulin or insulin analogue has a crystal size in the range of 1-40 μm.

3. The integrated process of claim 1, wherein the temperature inside the assemblage pressure filtration unit is maintained in the range of 25° C. to 35° C.

4. The integrated process of claim 1, wherein the pressure filtration unit comprises a filter membrane with a pore size in the range of 1-15 μm.

5. The integrated process of claim 1, wherein the single continuous process is completed within 5 to 10 minutes.

6. The integrated process of claim 1, wherein the filter fabric is placed on a stainless steel mesh support of the pressure filtration unit.

7. The integrated process of claim 1, wherein the filter fabric is selected from a poly ester fabric and poly propylene fabric.

8. The integrated process of claim 1 wherein the volume of the 100% organic solvent is 5-10% of the volume of the crystal suspension.

9. The integrated process of claim 1, wherein the 100% organic solvent is acetonitrile.

10. The integrated process of claim 1, wherein the process is conducted without relying on centrifugal force.

\* \* \* \* \*